United States Patent

Augstein et al.

[11] 4,029,802
[45] June 14, 1977

[54] THE TREATMENT OF ASTHMA, HAY FEVER OR URTICARIA

[75] Inventors: Joachim Augstein, Linford; Hugh Cairns, Loughborough; Dennis Hunter, Loughborough; John King, Loughborough, all of England

[73] Assignee: Fisons Limited, England

[22] Filed: Apr. 22, 1974

[21] Appl. No.: 463,180

Related U.S. Application Data

[62] Division of Ser. No. 175,391, Aug. 26, 1971, abandoned.

[30] Foreign Application Priority Data

Aug. 27, 1970 United Kingdom ............ 41225/70
July 1, 1971 United Kingdom ............ 30828/71

[52] U.S. Cl. .............................................. 424/269
[51] Int. Cl.² ........................................... A61K 31/41
[58] Field of Search ................ 424/269; 260/308 D

[56] References Cited

UNITED STATES PATENTS 3,671,625  6/1972  Altounyan .................... 424/330

OTHER PUBLICATIONS

Juby et al. I, J. Med. Chem. vol. 12, pp. 396–401 (1969).
Juby et al. II, J. Med. Chem., vol. 11 pp. 111–117 (1968).
Buchananan et al., J. Med. Chem., vol. 12 pp. 1001–1006 (1969).

Primary Examiner—Stanley J. Friedman

Attorney, Agent, or Firm—Wenderoth, Lind & Ponack

[57] ABSTRACT

There are described compounds of formula I,

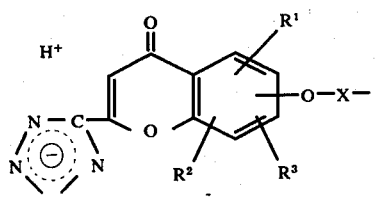

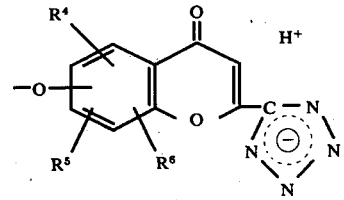

I and pharmaceutically acceptable derivatives thereof, in which $R^1$, $R^2$, $R^3$, $R^4$, $R^5$ and $R^6$ are the same or are different and each is a hydrogen or halogen atom or an alkyl, hydroxy, alkoxy, or substituted alkyl or alkoxy group, (for example a hydroxy-alkoxy, alkoxyalkoxy or carboxyalkoxy group), and X is a saturated or unsaturated, substituted or unsubstituted, straight or branched hydrocarbon chain which may be interrupted by a carbocyclic or heterocyclic ring, or by one or more oxygen atoms or carbonyl groups. There are also described processes for making the compounds and pharmaceutical compositions, for the treatment of asthma, containing the compounds.

7 Claims, No Drawings

THE TREATMENT OF ASTHMA, HAY FEVER OR URTICARIA

This is a divisional of Ser. No. 175,391, filed on Aug. 26, 1971, now abandoned.

This invention relates to new tetrazole derivatives, compositions containing them and methods for their preparation.

According to our invention we provide compounds of formula I,

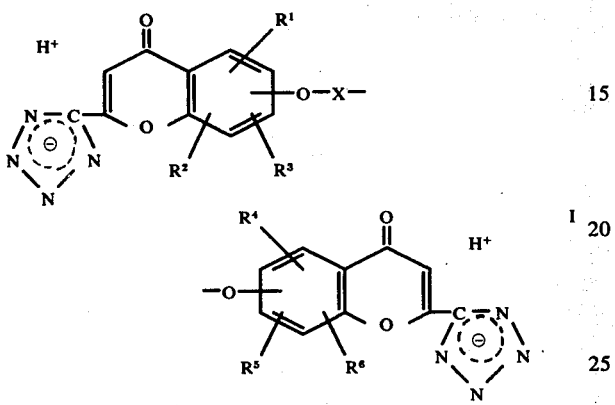

and pharmaceutically acceptable derivatives thereof, in which $R^1$, $R^2$, $R^3$, $R^4$, $R^5$ and $R^6$ are the same or are different and each is a hydrogen or halogen atom or an alkyl, hydroxy, alkoxy, or substituted alkyl or alkoxy group, (for example a hydroxy-alkoxy, alkoxyalkoxy or carboxyalkoxy group), and X is a saturated or unsaturated, substituted or unsubstituted, straight or branched hydrocarbon chain which may be interrupted by a carbocyclic or heterocyclic ring, or by one or more oxygen atoms or carbonyl groups.

In general, it is preferred that not more than one of $R^1$, $R^2$ and $R^3$, and not more than one of $R^4$, $R^5$, and $R^6$ is other than hydrogen.

Accordingly a preferred embodiment of the invention is for compounds of the formula Ia, In this specification and in the claims the term 'lower', e.g. as applied to alkyl or alkoxy groups, means that the group contains up to 6 carbon atoms.

Particularly preferred compounds according to the invention are those in which all of $R^1$, $R^2$, $R^3$, $R^4$, $R^5$ and $R^6$ are hydrogen.

The group X may be any of a wide variety of groups. Thus for example, it may be a substituted or unsubstituted, straight or branched, saturated or unsaturated hydrocarbon chain. Further, X may be such a chain interrupted by one or more oxygen atoms, carbonyl groups or by a carbocyclic or heterocyclic ring and may be substituted by one or more halogen atoms (e.g. chlorine or bromine atoms) or hydroxy or alkoxy groups. Specific examples of the groups X are groups of the formulae:

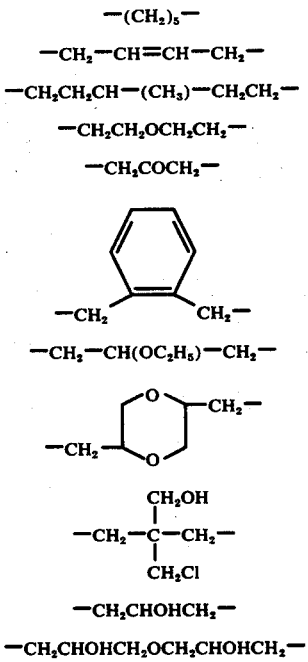

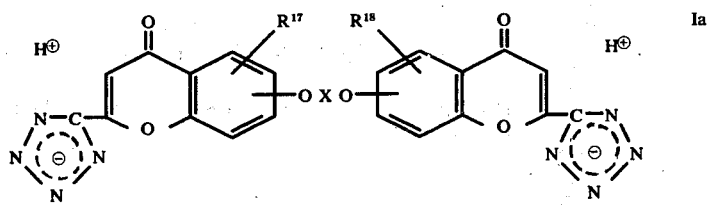

and pharmaceutically acceptable derivatives thereof, in which $R^{17}$ and $R^{18}$ are the same or are different and each is a hydrogen or halogen atom or an alkyl, hydroxy, alkoxy or substituted alkoxy group, and X has the meaning defined above.

Values of $R^1$, $R^2$, $R^3$, $R^4$, $R^5$ and $R^6$ which may be mentioned include hydrogen, chlorine, bromine, lower alkyl, hydroxy, lower alkoxy, hydroxy-lower alkoxy, lower alkoxy-lower alkoxy and carboxy-lower-alkoxy.

The group X is preferably a substituted or unsubstituted straight or branched hydrocarbon chain, which may be interrupted by one or more oxygen atoms, and contains from 3 to 7 carbon atoms. Desirably such a chain is substituted by one or more chlorine or hydroxyl groups; a particularly preferred chain being the 1-hydroxy-trimethylene chain ($-CH_2CHOHCH_2-$).

Thus, a further embodiment of the invention is for the bis-benzopyranyl compounds of the formula Ib,

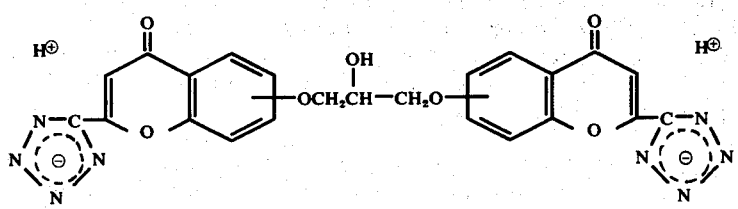

and pharmaceutically acceptable derivatives thereof. The chain —O—X—O may link different or corresponding positions on the benzopyrone nuclei.

Particularly preferred compounds according to the invention are those in which the —OXO— group links the 5,5' positions, e.g. the compound of formula Ic,

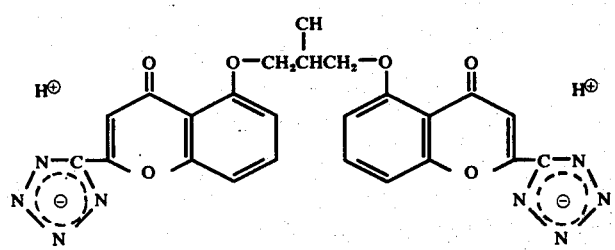

and pharmaceutically acceptable derivatives thereof.

According to our invention we also provide processes for the production of a compound of formula I, which comprise a. treating a compound of formula II,

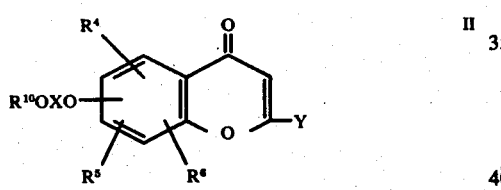

in which $R^4$, $R^5$, $R^6$ and X are as defined above, $R^{10}$ represents a group of formula III,

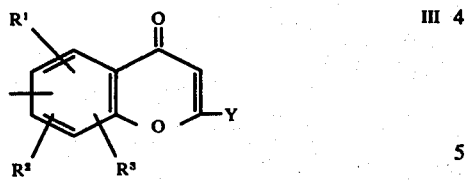

in which $R^1$, $R^2$ and $R^3$ are as defined above, or a group $R^7$ of formula IV,

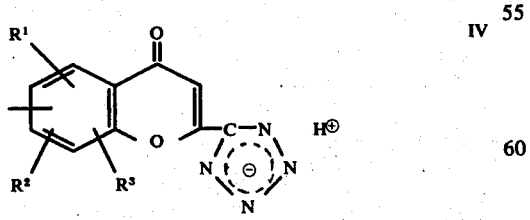

in which $R^1$, $R^2$ and $R^3$ are as defined above, Y represents a group —CN or —CZ=NH, and Z represents a good leaving group, with an azide in a solvent which is inert under the reaction conditions, b. replacing with hydrogen the group G in a compound of formula V or VI,

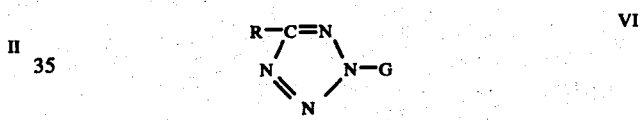

in which R represents a group of formula VII,

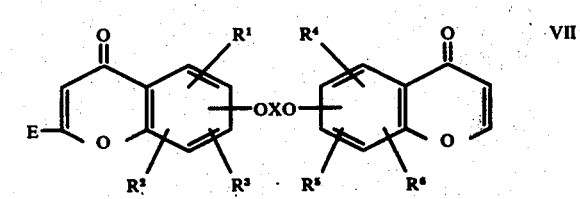

in which $R^1$, $R^2$, $R^3$, $R^4$, $R^5$, $R^6$ and X are as defined above,

E represents a tetrazole group or a group of formula VIII or IX,

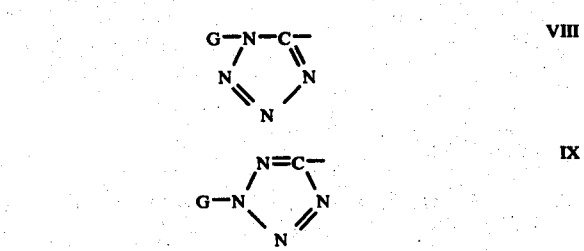

and G represents a group which may be replaced by hydrogen, by hydrogenation, dealkylation, deacylation, under mildly basic conditions, under acidic conditions, or by reductive deamination, c. cyclising a compound of formula X, or a salt thereof in which $R^4$, $R^5$, $R^6$ and X are as defined above, and
R' represents a group $R^7$, as defined above, or a group of formula XI, in which $R^1$, $R^2$ and $R^3$ are as defined above, selectively dehydrogenating a compound of formula XII, in which $R^4$, $R^5$, $R^6$ and X are as defined above, and R" represents a group $R^7$, as defined above, or a group of formula XIII, in which $R^1$, $R^2$ and $R^3$ are as defined above, or transforming a compound of formula XIV, in which $R^4$, $R^5$, $R^6$ and X are as defined above, and $R^8$ is a group $R^7$, as defined above, or a group of formula XV, in which $R^1$, $R^2$ and $R^3$ are as defined above, into a compound of formula I,
and where desired or necessary converting the compound of formula I produced by any one of processes (a) to (e) above to a pharmaceutically acceptable derivative thereof.

Suitable solvents which are inert under the reaction conditions of process (a) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130° C for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetramethylammonium, anilinium, morpholinium and piperdinium azides, may also be used if desired. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above the reaction may be carried out using hydrazoic acid (hydrogen azide) at a temperature of from about 20° to 150° C in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid. Process (a) is believed to pass through a compound of formula XIV as an intermediate. The good leaving group Z may be an alkoxy, thiol or alkylthio group, e.g. a lower alkoxy or a lower alkylthio group.

In process (b) the group G may be, for example, an aralkyl, e.g. a benzyl group; an aroylalkyl, e.g. a phenacyl group; an acyl, e.g. acetyl group; an amino group; or a group $-(CH_2)_2A$, where A is an electron withdrawing group, for example, a nitrile, a carboxylic ester, e.g. of a lower alkanol, or an acyl group, e.g. an acetyl group.

When G represents an aralkyl group the group may be replaced by using either a hydrogen halide, e.g. HBr, in acetic acid, or by catalytic hydrogenation using, for example, a palladium catalyst in a solvent which is inert under the reaction conditions, e.g. ethanol.

When G represents an acyl group, the group may be replaced under mildly basic conditions with, for example, aniline or sodium bicarbonate.

When G represents a group $-CH_2CH_2A$ the group may be replaced under mildly basic conditions with, for example, barium hydroxide.

When G represents an amino group, the group may be replaced by reductive de-amination with, for example, hypophosphorous acid, stannous chloride, or sodium in liquid ammonia.

The cyclisation of process (c) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. It will be appreciated that the compound of formula X may also exist in keto form, and this form is included in the definition of formula X. The compound of formula X may, if desired, be used in the form of an alkali metal salt thereof.

In process (d) the dehydrogenation may be carried out by oxidation using a mild oxidizing agent, for example selenium dioxide, palladium black, chloranil, lead tetraacetate or triphenylmethyl perchlorate. Alternatively the dehydrogenation may be carried out indirectly by halogenation followed by dehydrohalogenation, e.g. by treatment with N-bromosuccinimide or pyridinium bromide perbromide to yield the 3-bromo derivative which is subsequently dehydrobrominated. The reaction may be carried out in a solvent which is inert under the reaction conditions, e.g. a halogenated hydrocarbon, xylene or glacial acetic acid. The reaction may be carried out at any elevated temperature, e.g. from about 20° to 150° C.

The transformation of process (e) may be effected by warming in a solvent which is inert under the reaction conditions, e.g. ethanol. The reaction may be carried out under acidic or neutral conditions, but is preferably carried out in the presence of a base, e.g. sodium hydroxide, in a solvent which is inert under the reaction conditions, e.g. water or ethanol. The reaction is also preferably carried out in dilute, e.g. about 1%. solution and may be carried out at from about 15° to 35° C.

The compounds of formula II in which Y is a group —CN may be made by dehydrating the corresponding compound of formula XVI,

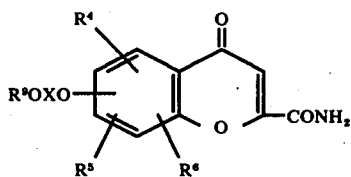

in which $R^4$, $R^5$, $R^6$ and X are as defined above, and $R^9$ is a group $R^7$, as defined above, or a group of formula XVII,

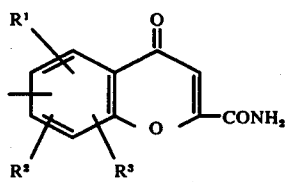

in which $R^1$, $R^2$ and $R^3$ are as defined above.

The reaction is preferably carried out using at least two molar equivalents of a dehydrating agent, e.g. $POCl_3$, per mole of compound of formula XVI. Where the dehydrating agent reacts with one of $R^1$ to $R^6$ or with X (e.g. with a group comprising an —OH group) sufficient dehydrating agent should be used to satify the side reaction as well as the main reaction, or the reactive group should be protected. The reaction may, if desired, be carried out in the presence of an acid binding agent, e.g. trimethylamine. The reaction may be carried out in the presence of a solvent, e.g. N,N-dimethylformamide, dimethyl sulphoxide, pyridine, benzene or hexamethyl phosphoramide, or an excess of the dehydrating agent may be used as the reaction medium. The reaction may be carried out at a temperature of from about 0° to 200° C depending on the dehydrating agent used. When phosphorus oxychloride is used a temperature of from 0° to 100° C is preferred.

The compounds of formula XVI may be made by reacting a compound of formula XVIII,

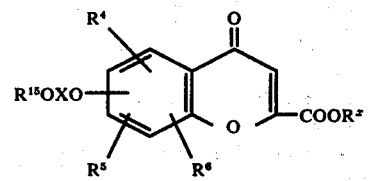

in which $R^4$, $R^5$, $R^6$ and X are as defined above, $R^x$ is a lower alkyl group, and $R^{15}$ is a group $R^7$, as defined above, or a group of formula XIX,

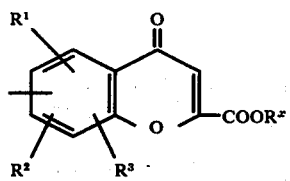

in which $R^1$, $R^2$, $R^3$ and $R^x$ are as defined above, with ammonia, using techniques conventional in the production of amides from esters, e.g. using an alkanol as solvent at a temperature of 0° to 120° C.

Compounds of formula II in which Y is a group -CZ=NH may be made in a manner known per se from compounds of formula II in which Y is a group —CN, e.g. by reaction with an alkanol, a thiol or $H_2S$ in the presence of HCl.

Compounds of formula V may be made by reacting a compound of formula XX,

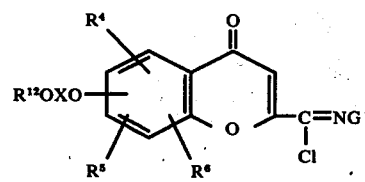

in which $R^4$, $R^5$, $R^6$, X and G are as defined above, and $R^{12}$ is a group $R^7$, as defined above, or a group of formula XXI,

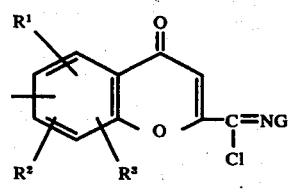

in which $R^1$, $R^2$, $R^3$ and G are as defined above, with an azide. The reaction may be carried out under substantially the same conditions as set out above for process (a).

The compounds of formula XX may be made by reacting a compound of formula XXII,

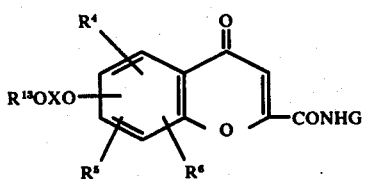

XXII in which $R^4$, $R^5$, $R^6$, X and G are as defined above, and $R^{13}$ is a group $R^7$, as defined above, or a group of formula XXIV,

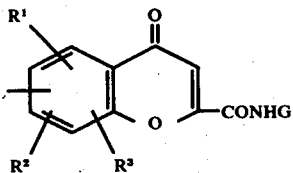

XXIV in which $R^1$, $R^2$, $R^3$ and G are as defined above, with phosphorous pentachloride.

The compounds of formulae V and VI may also be made from a compound of formula I using techniques known per se, for example by reaction with a compound G Hal, in which G is as defined above and Hal represents a halogen atom, using techniques conventional in similar reactions. Compounds of formulae V and VI in which G is an amino group may be made by reacting a compound of formula I with hydroxylamine-O-sulphonic acid in weakly aqueous alkaline solution and compounds of formula V and VI in which G is a group —$CH_2CH_2A$ may also be made by Michael addition of a compound $CH_2$=CHA to a compound of formula I.

The compounds of formula X may be made by reacting a compound of formula XXV,

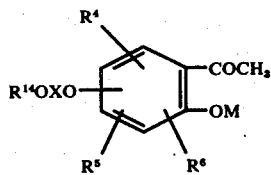

XXV in which $R^4$, $R^5$, $R^6$, X and M are as defined above, and $R^{14}$ represents a group $R^7$, as defined above, or a group of formula XXVI,

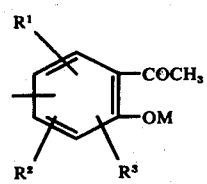

XXVI in which $R^1$, $R^2$, $R^3$ and M are as defined above, with a compound of formula XXVII,

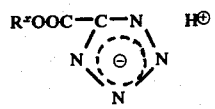

XXVII in which $R^x$ is as defined above. The reaction may be carried out under conditions conventional for a Claisen condensation. Compounds of formula X may also be made by the action of mild alkali on a compound of formula I.

Compounds of formula XII may be made by selective hydrogenation of a compound of formula I or by methods analagous to process (a) above using the corresponding chromanone-2-carboxylic acid (via the nitrile) as starting material.

The starting materials for the above processes are either known compounds or may be made from known compounds using known techniques or the techniques described above.

Some of the groups $R^1$, $R^2$, $R^3$, $R^4$, $R^5$, $R^6$ and X may be affected by the reaction conditions (either in the final steps or in the production of intermediates) described above. It is therefore contemplated that where necessary or desirable the reactions be carried out using protected derivatives of the reagents. Thus when free —OH groups are present they may be protected, for example by acylation and the protecting group removed subsequently, e.g. by hydrolysis.

It will be appreciated that while the unsubstituted tetrazole group has been represented above in a delocalised form other representations of the same group are also commonly used.

The compounds of formula I and the intermediates therefore may be recovered from their reaction mixtures using conventional methods.

The processes described above may produce the compound of formula I or a derivative thereof. It is also within the scope of this invention to treat any derivative so produced to liberate the free compound of formula I, or to convert one derivative into another. Pharmaceutically acceptable derivatives include pharmaceutically acceptable salts and notably water-soluble salts. Salts which may be mentioned include basic addition salts, e.g. ammonium salts, amine salts, alkali-metal and alkaline-earth metal salts, notably the sodium salt.

According to the invention there is also provided a process for the production of a pharmaceutically acceptable salt of a compound of formula I, which comprises treating a compound of formula I, or another salt thereof, with a compound, e.g. a base or ion exchange resin, containing an available pharmaceutically acceptable cation, e.g. sodium, potassium, calcium, ammonium and appropriate nitrogen containing cations. In general we prefer to form the pharmaceutically acceptable salt by treating the free acid of formula I with an appropriate base, e.g. with an alkaline-earth or alkali metal hydroxide, carbonate or bicarbonate in aqueous solution or by a metathetical process. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen. e.g. the combination the reaginic antibody with specific antigen (see Example A). In man, both subjective and objective changes which result from the inhalation of specific antigen by sensitised subjects are inhibited by prior administration of the compounds. Thus the compounds are useful in the treatment of asthma, e.g. allergic asthma. The compounds are also useful in the treatment of so-called 'intrinsic' asthma (in which no sensitivity to extrinsic antigen can be demonstrated). The compounds are also of value in the treatment of other conditions in which antigen-antibody reactions are responsible for disease, for example, hay fever and urticaria. For the abovementioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example A. For man the total daily dosage is in the range of from about 1 mg to 3,500 mg which may be administered in divided doses from 1 to 6 times a day or in sustained release form. Thus dosage forms suitable for administration (by inhalation or oesophageally) comprise from about 0.17 mg to 600 mg of the compound admixed with a solid or liquid pharmaceutically acceptable diluent or carrier. The compounds of formula I and pharmaceutically acceptable derivatives thereof may be administered by conventional techniques, preferably in admixture with a major proportion of a pharmaceutically acceptable diluent, adjuvant or carrier. Specifically the compounds may be administered by inhalation as a liquid, e.g. an aerosol composition, or as a powder composition, e.g. a powder composition containing a diluent such as lactose, and optionally in combination with a bronchodilator, e.g. isoprenaline, or oesophageally or a tablet or capsule.

For administration by inhalation we prefer to use a powder comprising particles of the compound of formula I, or a pharmaceutically acceptable derivative thereof, having an effective particle size in the range 0.01 to 10 microns, preferably in combination with a coarse carrier, e.g. having an effective particle size in the range 30 to 80 microns. The fine particles of the compound of formula I, or of the pharmaceutically acceptable derivative thereof, may be made by grinding or milling the compound of formula I, or the pharmaceutically acceptable derivative thereof.

The invention is illustrated by the following Examples in which the parts are by weight.

EXAMPLE 1

5,5'-[(2-Hydroxytrimethylene)dioxy]bis[5-(4-oxo-4H-1-benzopyran-2-yl)tetrazole]

a. 5,5'-[(2-Hydroxytrimethylene)dioxy]bis[4-oxo-4H-1-benzopyran-2-carboxamide]

A suspension of 25 parts of 5,5'-[(2-hydroxytrimethylene)dioxy]bis[4-oxo-4H-1-benzopyran-2-carboxylic acid] diethyl ester in 250 parts of N,N-dimethylformamide and 250 parts of 0.88 ammonium hydroxide solution was stirred at room temperature for four hours. The resulting reaction mixture was filtered, the residue was washed with water and then dried to give 23 parts of a white powder m.p. 288°-294° C (decomp.). Crystallisation of this product from aqueous N,N-dimethylformamide gave 20 parts of 5,5'-[(2-hydroxytrimethylene)dioxy[bis[4-oxo-4H-1-benzopyran-2-carboxamide] as white crystals m.p. 293°-295° C (decomp.).

Spectral confirmation

The i.r. spectrum (nujol mull) contained bands at 1700 and 1640cm$^{-1}$ due to the amide carbonyl group and the benzopyran ring carbonyl group, respectively. In addition, it contained bands at 3150 and 3280 cm$^{-1}$ due to the amide N-Hs. The n.m.r. spectrum included peaks at 1.56 and 1.90% due to the 2 N-H protons of the amide group and also a singlet at 3.38% due to the benzopyran ring 3-proton (solvent: dimethylsulphoxide — d$_6$).

b. 5,5'-[(2-Formyloxytrimethylene)dioxy]bis[4-oxo-4H-1-benzopyran-2-carbonitrile]

To 250 parts of N,N-dimethylformamide was slowly added 10 parts of phosphorus oxychloride with stirring and ice-cooling. Then, in small quantities, 20 parts of 5,5'-[(2-hydroxytrimethylene)dioxy]bis[4-oxo-4H-1-benzopyran-2-carboxamide] were added to the solution and the reaction mixture was stirred at room temperature for 72 hours. The resulting dark solution was poured into 1000 parts of ice/water and the precipitated solid was filtered, washed with water and dried to give 16 parts of a light brown powder. Crystallisation of this product from a mixture of ethanol and N,N-dimethylformamide gave 14 parts of 5,5'-[(2-formyloxytrimethylene)dioxy]bis[4-oxo-4H-1-benzopyran-2-carbonitrile] as white crystals m.p. 214°-216° C (decomp.).

Spectral confirmation

The i.r. spectrum (nujol mull) contained a doublet at 1735cm.$^{-1}$ due to the formate carbonyl group and a band at 1655cm.$^{-1}$ due to the benzopyran ring carbonyl group. The n.m.r. spectrum included sharp singlets at 1.32 and 2.7% due to the proton of the formate group and the benzopyran ring 3-proton, respectively (solvent: dimethylsulphoxide - d$_6$).

c. 5,5'-[(2-Hydroxytrimethylene)dioxy]bis[5-(4-oxo-4H-1-benzopyran-2-yl)tetrazole]

A mixture of 18 parts of 5,5'[(2-formyloxytrimethylene)dioxy]bis[4-oxo-4H-1-benzopyran-2-carbonitrile], 7.5 parts of sodium azide, 6 parts of ammonium chloride and 200 parts of N,N-dimethylformamide were stirred and heated on a steam bath for 48 hours. Most of the solvent was then removed by distillation under reduced pressure and 200 parts of water were added to the residue. The suspension thus produced was filtered and the filtrate was acidified with 20% hydrochloric acid to give a precipitate which was filtered, washed with water and dried to give 15 parts of 5,5'-[(2-hydroxytrimethylene)dioxy]bis[5-(4-oxo-4H-1-benzopyran-2-yl)tetrazole] as a yellow solid.

A portion of this product was purified by converting it to its disodium salt with aqueous sodium bicarbonate and then reconverting this salt back to the free tetrazole with hydrochloric acid giving a yellow solid, m.p. 300° (decomp.).

Analysis: Found: C, 53.22; H, 3.56; N, 21.01%; C$_{23}$H$_{16}$N$_8$O$_7$ requires: C, 53.49; H, 3.12; N, 21.71%

Spectral confirmation

The i.r. spectrum (nujol mull) contained a band at 1655cm.$^{-1}$ due to the benzopyran ring carbonyl group.

The n.m.r spectrum included a broad absorption at 4.49Y due to the protons of the 2 N—H and O—H groups and also a singlet at 3.23Y due to the benzopyran ring 3-proton (solvent: dimethylsulphoxide - d$_6$).

5,5'-[(2-Hydroxytrimethylene)dioxy]bis[5-(4-oxo-4H-1-benzopyran-2-yl)tetrazole], disodium salt 17.45 Parts of 5,5'-[(2-hydroxytrimethylene)dioxy]-bis[5-(4-oxo-4H-1benzopyran-2-yl)-tetrazole] were dissolved, with warming, in a solution of 5.11 parts of sodium bicarbonate in 400 parts of water. The water was azeotroped from the resulting solution, using isopropyl alcohol, until a solid was precipitated. This solid was filtered, washed with cold water and dried to give 8.5 parts of 5,5'-[(2-hydroxytrimethylene) dioxy]-bis[5-(4-oxo-4H-1-benzopyran-2-yl)tetrazole], disodium salt sesquihydrate as a pale yellow powder.

Analysis: Found: C, 46.74; H, 3.18; N, 18.32%; $C_{23}H_{14}N_8O_7Na_2 \cdot 1½H_2O$ requires: C, 47.02; H, 2.97; N, 18.96%

Spectral confirmation

The i.r. spectrum (nujol mull) contained a peak at 1658cm.$^{-1}$ due to the benzopyran ring carbonyl group. The n.m.r spectrum included a singlet at 3.28Y due to the benzopyran ring 3-proton (solvent: dimethylsulphoxide - $d_6$).

EXAMPLE 2

5,5'-[(2-Chlorotrimethylene)dioxy]bis[5-(4-oxo-4H-1-benzopyran-2-yl)tetrazole]

a. 5,5'-[(2-Chlorotrimethylene)dioxy]bis[4-oxo-4H-1-benzopyran-2-carboxylic acid], diethyl ester A mixture of 24.5 parts of 5,5'-[(2-hydroxytrimethylene)dioxy]bis [4-oxo-4H-1-benzopyran-2-carboxylic acid] diethyl ester and 47.6 parts of thionyl chloride in 40 parts of dry 1,2-dichloroethane was refluxed for 16 hours. The solvent was then evaporated, the residue was triturated with petrol and the resulting solid was crystallized from ethanol to give 15.6 parts of 5,5'-[(2-chlorotrimethylene)dioxy]bis[4-oxo-4H-1-benzopyran-2-carboxylic acid], diethyl ester as white crystals m.p. 144°–144.5° C.

Analysis:
Found: C, 60.08; H, 4.33; $C_{27}H_{23}O_{10}Cl$ required: C, 59.74; H, 4.27

Spectral confirmation

The i.r. spectrum (nujol mull) contained bands at 1730 and 1670cm$^{-1}$ due to the ester carbonyl group and the benzopyran ring carbonyl group, respectively. The n.m.r. spectrum included a peak at 5.30τ due to the trimethylene protons and also a singlet at 3.13τ due to the benzopyran ring 3-proton (solvent: deuterochloroform). The mass spectrum showed a molecular ion at m/e 542, with an isotope peak at m/e 544 due to the presence of the chlorine atom.

5,5'-[(2-Chlorotrimethylene)dioxy]bis[4-oxo-4H-1-benzopyran-2-carboxamide]

A suspension of 15 parts of 5,5'-[(2-chlorotrimethylene)dioxy]bis[4-oxo-4H-1-benzopyran-2-carboxylic acid], diethyl ester in 150 parts of N,N-dimethylformamide and 150 parts of 0.88 ammonium hydroxide solution was stirred at room temperature for 5 hours. The resulting reaction mixture was filtered, the residue was washed with water and then dried to give 11 parts of a white powder. Crystallisation of this product from aqueous N,N-dimethylformamide gave 8 parts of 5,5'-[(2-chlorotrimethylene)dioxy]bis[4-oxo-4H-1-benzopyran-2-carboxamide] as white crystals, m.p. 175° C (decomp.), giving a positive Beilstein's halogen test.

Spectral confirmation

The i.r. spectrum (nujol mull) contained bands at 1705 and 1655cm$^{-1}$ due to the amide carbonyl and benzopyran ring carbonyl groups, respectively. In addition it contained bands at 3200 and 3320cm$^{-1}$ due to the amide N-Hs.

5,5'-[(2-Chlorotrimethylene)dioxy]bis[4-oxo-4H-1-benzopyran-2-carbonitrile]

To 120 parts of N,N-dimethylformamide was slowly added 5 parts of phosphorous oxychloride with stirring and ice-cooling. Then 10 parts of 5,5'-[(2-chlorotrimethylene) dioxy]bis[4-oxo-4H-1-benzopyran-2-carboxamide] were added to the solution, in small quantities, and the reaction mixture was stirred at room temperature for 60 hours. The resulting dark solution was poured into 500 parts of ice/water and the precipitated solid was filtered, washed with water and dried to give 6.8 parts of a brown powder. Crystalisation of this product from a mixture of ethanol and N,N-dimethylformamide gave 4.6 parts of 5,5'-[(2-chlorotrimethylene)dioxy]bis[4-oxo-4H-1-benzopyran-2-carbonitrile] as white crystals, m.p. 185° C (decomp.), giving a positive Beilstein's halogen test.

Spectral confirmation

The i.r. spectrum (nujol mull) contained a peak at 1660cm$^{-1}$ due to the benzopyran ring carbonyl group.

5,5'-[(2-chlorotrimethylene)dioxy]bis[5-(4-oxo-4H-1-benzopyran-2-yl)tetrazole]

A mixture of 6 parts of 5,5'-[(2-chlorotrimethylene)-dioxy]bis[4-oxo-4H-1-benzopyran-2-carbonitrile], 2.2 parts of sodium azide, 1.8 parts of ammonium chloride and 60 parts of N,N-dimethylformamide were stirred and heated on a steam bath for 30 hours. Most of the solvent was then removed by distillation under reduced pressure and 60 parts of water were added to the residue. The insoluble material was filtered and the filtrate was acidified with 20% hydrochloric acid to give a precipitate which was washed with water and dried to give 4.8 parts of 5,5'-[(2-chlorotrimethylene)dioxy]-bis[5-(4-oxo-4H-1-benzopyran-2-yl)tetrazole] as a yellow solid.

A portion of this product was purified by converting it to it's disodium salt with aqueous sodium bicarbonate and then reconverting this salt back to the free tetrazole with hydrochloric acid giving a yellow solid, m.p. 245° C (decomp.), which gave a positive Beilstein's halogen test.

Spectral confirmation

The i.r. spectrum (nujol mull) contained a band at 1658cm$^{-1}$ due to the benzopyran ring carbonyl group. The n.m.r. spectrum included a broad absorbtion at 3.40τ due to the protons of the 2N-H groups, a multiplet at 5.27τ due to the trimethylene protons and also a singlet at 3.12τ due to the benzopyran ring 3-proton (solvent:dimethylsulphoxide - $d_6$).

e. 5,5'-[(2-Chlorotrimethylene)dioxy]bis[5-(4-oxo-4H-1-benzopyran-2-yl)-tetrazole], disodium salt 3.20 Parts of 5,5'-[(2-chlorotrimethylene)dioxy]-bis[5-(4-oxo-4H-1-benzopyran-2-yl)-tetrazole] were dissolved, with warming, in a solution of 1.01 parts of sodium bicarbonate in 60 parts of water. The water was azeotroped from the resulting solution, using iso-propyl alcohol, until a solid was precipitated. This solid was filtered, washed with cold water and dried to give 1.8 parts of 5,5'-[(2-chlorotrimethylene)dioxy]bis[5-(4-oxo-4H-1-benzopyran-2-yl)tetrazole], disodium salt as a yellow powder.

Spectral confirmation

The i.r. spectrum (nujol mull) contained a peak at 1655cm$^{-1}$ due to the benzopyran ring carbonyl group.

EXAMPLE 3

5,5'-[(2-Hydroxytrimethylene)dioxy]bis[5-(4-oxo-4H-1-benzopyran-2-yl)tetrazole]

A solution of 0.52 parts of 5,5'-[(2-hydroxytrimethylene) dioxy]bis[5-(2,3-dihydro-4-oxo-4H-1-benzopyran-2-yl)tetrazole]and 0.88 parts of selenium dioxide in 10 parts of N.N-dimethylformamide was heated at 85° to 90°, with stirring, for 3 hours. After cooling, the reaction mixture was filtered, and the filtrate poured into water. The suspension thus produced was filtered, washed with water and dried to give 5,5'-[(2-hydroxytrimethylene) dioxy]bis[5-(4-oxo-4H-1-benzopyran-2-yl)tetrazole] as a yellow solid, m.p. 300° (decomp.).

EXAMPLE A

The procedure set out below may be used to assess the effectiveness of a compound in inhibiting the release of the pharmacological mediators of anaphylaxis.

In this test, the effectiveness of the compounds in inhibiting the passive cutaneous anaphylactic reaction in rats is assessed. It has been proved that this form of test gives reliable qualitative indications of the ability of the compounds under test to inhibit antibody-antigen reactions in man.

In this test method Charles River France/Fisons bred rats (male or female) having a body weight of from 100 to 150 gms are infected subcutaneously at weekly intervals with N. brasiliensis larvae in doses increasing from about 2000 larvae per animal to 12000 larvae per animal in order to establish the infection. After 8 weeks the rats are bled by heart puncture and 15-20 mls. of blood collected from each animal. The blood samples are then centrifuged at 3500 rpm. for 30 minutes in order to remove the blood cells from the blood plasma. The serum is collected and used to provide a serum containing N. brasiliensis antibody. A pilot sensitivity test is carried out to determine the least quantity of serum required to give a skin weal in control animals in the test described below of 2 cm diameter. It has been found that optimum sensitivity of rats in the body weight range 100-130 100-130 is obtained using a serum diluted with eight parts of physiological saline solution. This diluted solution is called antibody serum A.

The antigen to react with the antibody in serum A is prepared by removing N, brasiliensis worms from the gut of the infested rats, centrifuging the homogenate and collecting the supernatent liquor. This liquor is diluted with saline to give a protein content of 1 mg/ml and is known as solution B.

Charles River France/Fisons bred rats in the body weight range 100 to 130 gms are sensitised by intradermal injection of 0.1 mls of serum A into the right flank. Sensitivity is allowed to develop for 24 hours and the rats are then injected intravenously with 1 ml/100 gms body weight of a mixture of solution B (0.25 mls.) Evans Blue dye solution (0.25 mls) and the solution of the compound under test (0.5 mls with varying percentages of active matter). Insoluble compounds are administered as a separate intraperitoneal injection 5 minutes before intravenous administration of solution B and Evans Blue dye. For each percentage level of active matter in the solution under test five rats are injected. Five rats are used as controls in each test. The dosages of the compound under test are selected so as to give a range of inhibition values.

Thirty minutes after injection of solution B the rats are killed and the skins are removed and reversed. The intensity of the anaphylactic reaction is assessed by comparing the size of the characteristic blue weal produced by the spread of the Evans Blue dye from the sensitisation site, with the size of the weal in the control animals. The size of the weal is rated as 0 (no weal detected, i.e. 100% inhibition) to 4 (no difference in size of weal, i.e. no inhibition) and the percentage inhibition for each dose level calculated as:

$$\% \text{ inhibition} = \frac{(\text{Control group score} - \text{treated group score}) \times 100}{\text{Control group score}}$$

The percentage inhibitions for the various dose levels are plotted graphically for each compound. From these graphs the dosage required to achieve a 50% inhibition of the anaphylactic reaction ($ID_{50}$) may be determined.

The compounds are also evaluated in the above manner using intestinal and gastric administration of the compound.

EXAMPLE B

An inhalation composition comprises a mixture of 20 mg of a compound of formula I, e.g., 5,5'-[(2-hydroxytrimethylene) dioxy]bis[5-(4-oxo-4H-1-benzopyran-2-yl)tetrazole] disodium salt, of effective particle size 1 to 10 microns and 20 mg of crystalline lactose of effective particle size 32 to 63 microns. The composition may be put up in a gelatin capsule.

We claim:

1. A method of treatment of asthma, hay fever or urticaria, which comprises administering a theraputically effective amount for the treatment of asthma, hay fever or urticaria, of a compound selected from a compound of formula I,

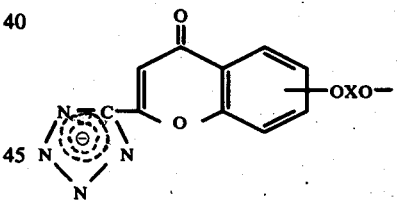
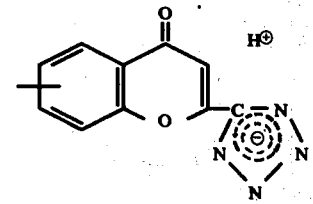

wherein X represent a hydrocarbon chain containing from 3 to 7 carbon atoms which chain may be substituted by one or more hydroxy groups or chlorine atoms,
and a pharmaceutically acceptable salt thereof.
to a patient afflicted with asthma, hay fever or urticaria.

2. A method according to claim 1, wherein the compound to be administered is 5,5'-[(2-hydroxytrimethylene)dioxy]bis[5-(4-oxo-4H-1-benzopyran-2-yl)] tetrazole or a pharmaceutically acceptable salt thereof.

3. A method according to claim 1, wherein the compound to be administered is the di-sodium salt of 5,5'-

[(2-hydroxytrimethylene) dioxy]bis[5-(4-oxo-4H-1-benzopyran-2-yl)]tetrazole.

4. A method according to claim 1, which comprises administration of a daily dosage of from 1 mg to 3,500 mg of the compound of formula I, or of the pharmaceutically acceptable salt thereof.

5. A method according to claim 1, which comprises administering a unit dosage of from 0.17 mg to 600 mg of the compound of formula I or of the pharmaceutically acceptable salt thereof.

6. A method according to claim 1, wherein the compound of formula I or the pharmaceutically acceptable salt thereof is administered by inhalation.

7. A method according to claim 1 wherein the compound of formula I or salt thereof is admixed with lactose, as a carrier.

* * * * *